(12) United States Patent
Idowu et al.

(10) Patent No.: US 8,784,300 B2
(45) Date of Patent: Jul. 22, 2014

(54) DEVICES, SYSTEMS, AND METHODS FOR REMOVING EMPYEMA FROM A PLEURAL CAVITY

(75) Inventors: Olajire Idowu, Lafayette, CA (US); Sunghoon Kim, San Ramon, CA (US)

(73) Assignee: Children's Hospital & Research Center Oakland, Oakland, CA (US)

( * ) Notice: Subject to any disclaimer, the term of this patent is extended or adjusted under 35 U.S.C. 154(b) by 102 days.

(21) Appl. No.: 13/364,876

(22) Filed: Feb. 2, 2012

(65) Prior Publication Data
US 2012/0253113 A1 Oct. 4, 2012

Related U.S. Application Data

(60) Provisional application No. 61/469,575, filed on Mar. 30, 2011.

(51) Int. Cl.
*A61B 1/00* (2006.01)

(52) U.S. Cl.
USPC ............. 600/104; 600/114; 600/156; 604/22; 604/36

(58) Field of Classification Search
CPC ........... A61B 1/00119; A61B 1/00128; A61B 1/00135; A61B 1/018; A61B 1/273; A61B 5/150167; A61B 5/150442
USPC ........ 600/104, 156; 606/114–115; 604/22, 36
See application file for complete search history.

(56) References Cited

U.S. PATENT DOCUMENTS

| | | | |
|---|---|---|---|
| 4,692,139 A | 9/1987 | Stiles | |
| 4,998,527 A * | 3/1991 | Meyer | 600/104 |
| 5,441,503 A * | 8/1995 | Considine et al. | 606/115 |
| 5,499,970 A | 3/1996 | Olson | |
| 5,520,635 A | 5/1996 | Gelbfish | |
| 5,685,838 A | 11/1997 | Peters et al. | |
| 5,749,858 A | 5/1998 | Cramer | |
| 5,947,995 A | 9/1999 | Samuels | |
| 5,957,881 A | 9/1999 | Peters et al. | |
| 6,032,673 A * | 3/2000 | Savage et al. | 128/898 |
| 6,110,127 A * | 8/2000 | Suzuki | 600/565 |
| 6,159,209 A * | 12/2000 | Hakky | 606/45 |
| 6,293,957 B1 | 9/2001 | Peters et al. | |
| 6,358,197 B1 * | 3/2002 | Silverman et al. | 600/29 |
| 6,394,996 B1 | 5/2002 | Lawrence et al. | |
| 6,428,498 B2 * | 8/2002 | Uflacker | 604/22 |
| RE38,018 E * | 3/2003 | Anctil et al. | 606/170 |
| 6,682,505 B2 | 1/2004 | Bates et al. | |

(Continued)

OTHER PUBLICATIONS

Gyrus ENT, LLC (2002) "Diego Powered Dissector" Diego System Product Brochure.

*Primary Examiner* — Matthew J Kasztejna
(74) *Attorney, Agent, or Firm* — Benjamin C. Pelletier; Carol L. Francis; Bozicevic, Field & Francis LLP

(57) ABSTRACT

Pleural empyema removal devices are provided and enable the removal of empyema from the pleural cavity of a human or veterinary patient. The pleural empyema removal devices may be coupled with one or more additional devices, such as suction source, gas source, light source and/or camera source, and monitor. The devices and systems including the devices facilitate the removal of empyema from the pleural cavity of a patient while providing protections from damage to untargeted tissues. The devices, systems, and methods can be used in the treatment process to treat pleural empyema resulting from pleural effusions and infections stemming from various illnesses and disorders, such as pneumonia.

48 Claims, 11 Drawing Sheets

(56) References Cited

U.S. PATENT DOCUMENTS

| | | |
|---|---|---|
| 6,830,556 B2 | 12/2004 | Harmon et al. |
| 6,872,204 B2 * | 3/2005 | Houser .......................... 606/37 |
| 6,878,142 B2 | 4/2005 | Lawrence et al. |
| 6,994,705 B2 * | 2/2006 | Nobis et al. .................... 606/37 |
| 7,017,581 B2 | 3/2006 | Boyd et al. |
| 7,166,103 B2 | 1/2007 | Carmel et al. |
| 7,763,010 B2 | 7/2010 | Evans et al. |
| 2002/0010416 A1 * | 1/2002 | Uflacker ........................ 604/35 |
| 2002/0022796 A1 | 2/2002 | Lawrence et al. |
| 2003/0065321 A1 | 4/2003 | Carmel et al. |
| 2003/0130613 A1 | 7/2003 | Harmon et al. |
| 2003/0204200 A1 | 10/2003 | Rufener |
| 2004/0092895 A1 | 5/2004 | Harmon |
| 2004/0122447 A1 | 6/2004 | Harmon et al. |
| 2005/0070763 A1 * | 3/2005 | Nobis et al. ................... 600/114 |
| 2006/0173244 A1 * | 8/2006 | Boulais et al. ................ 600/156 |
| 2010/0217237 A1 | 8/2010 | Itou et al. |
| 2010/0228267 A1 | 9/2010 | Mercado |

\* cited by examiner

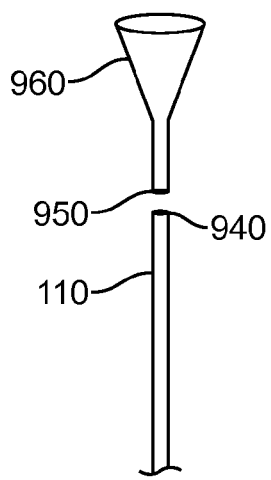 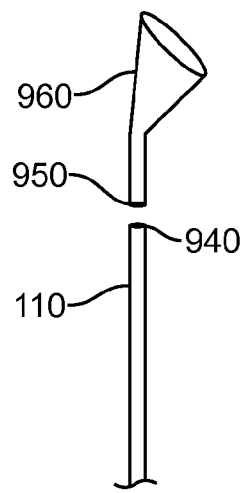 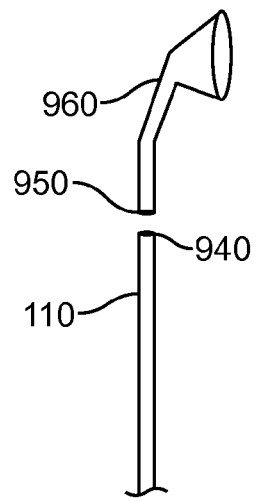
FIG. 7A  FIG. 7B  FIG. 7C
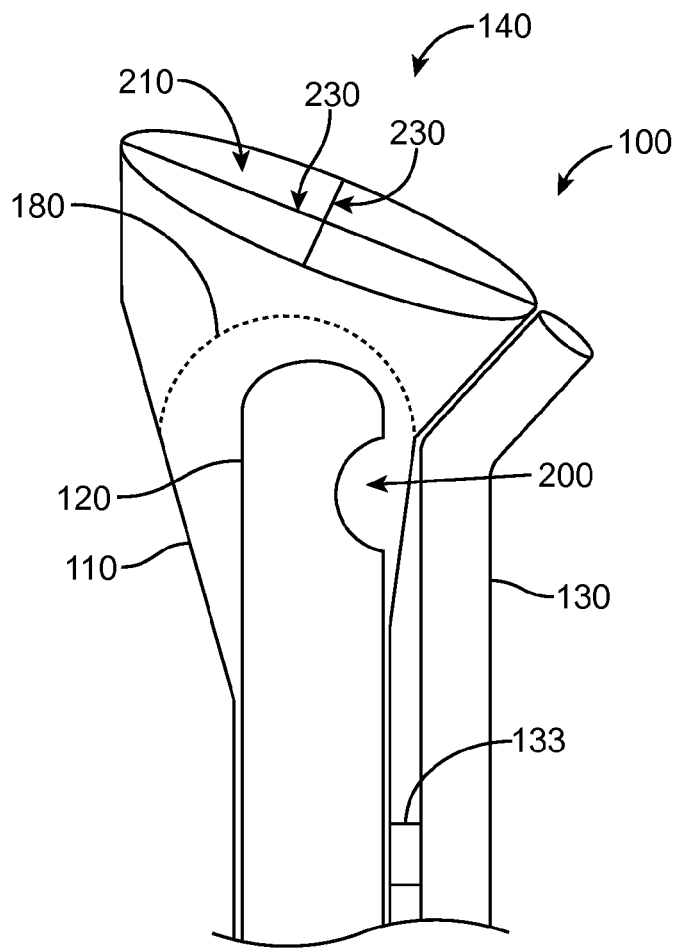
FIG. 6

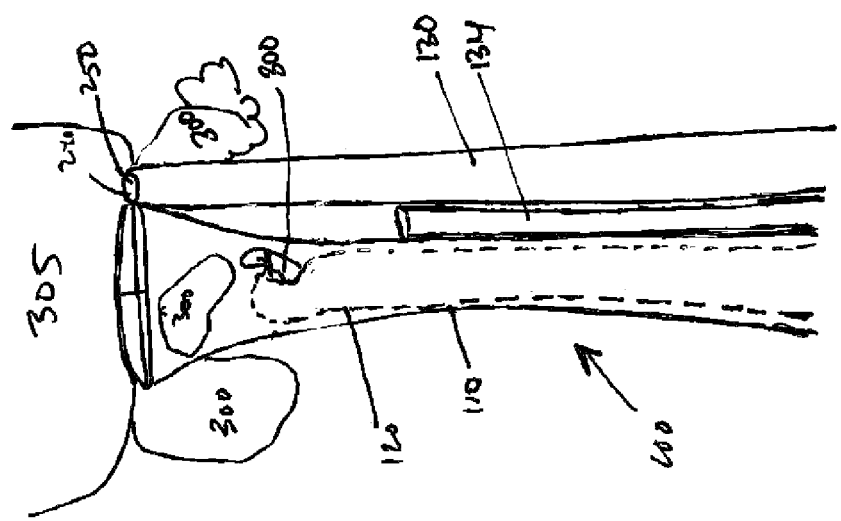
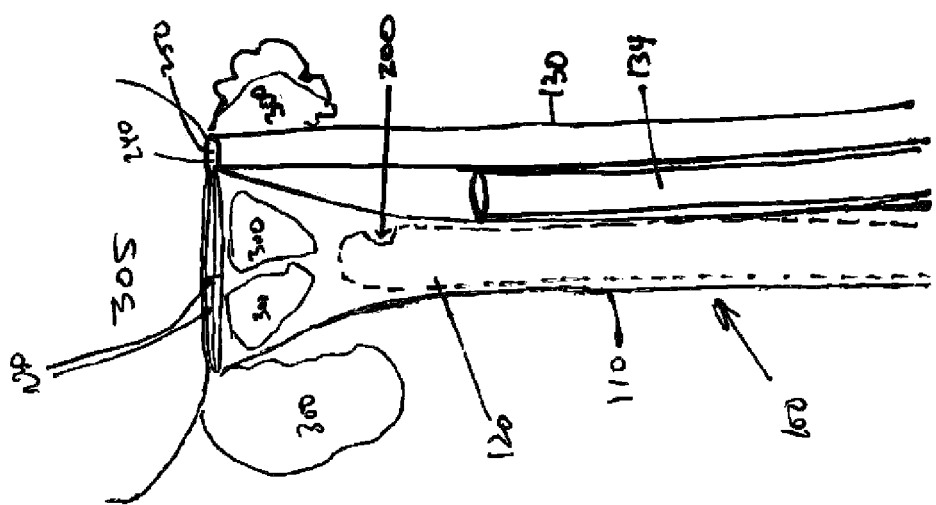
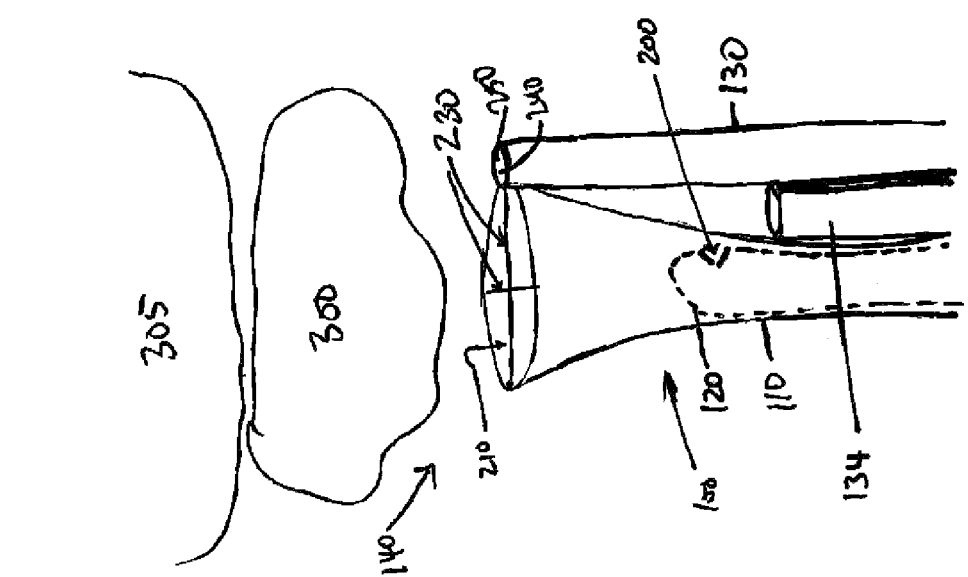

DEVICES, SYSTEMS, AND METHODS FOR REMOVING EMPYEMA FROM A PLEURAL CAVITY

CROSS-REFERENCE TO RELATED APPLICATION

This application claims the benefit of priority under 35 U.S.C. §119(e) to U.S. Provisional Application No. 61/469,575 filed Mar. 30, 2011, the disclosure of which is incorporated by reference herein in its entirety.

INTRODUCTION

FIG. 1 illustrates a partial cutaway view of a human chest cavity. As shown, the chest cavity 10 of subject 5 includes lungs 15. Pleura 20 is a serous membrane surrounding the lung 15 which folds back onto itself to form a two-layered, membrane structure. The thin space between the two pleural layers is the pleural cavity 25. The outer pleura (parietal pleura) is attached to the chest wall. The inner pleura (visceral pleura) covers the lungs and adjoining structures—e.g., blood vessels, bronchi and nerves. The pleura 20 and pleura cavity 25 are positioned in the chest cavity between the lung 15 and outer structure of the chest cavity, which is shown comprising muscle 30, ribs 35, fat 45, and skin 40.

The pleural cavity 25 and pleura 20 aid optimal functioning of the lungs 15 during respiration. The pleural cavity 25 also contains pleural fluid, which allows the pleura 20 to slide effortlessly against each other during ventilation. Surface tension of the pleural fluid also leads to close apposition of the lung surfaces with the chest wall. This physical relationship allows for optimal inflation of the alveoli during respiration. The pleural cavity 25 transmits movements of the chest wall to the lungs, particularly during heavy breathing. This occurs because the closely opposed chest wall transmits pressures to the visceral pleural surface and hence to the lung 15 itself.

Pleural empyema is pus and debris in the space between the lungs and the chest wall known as the pleural cavity. Pus accumulates in the pleural cavity in the chest pushing against the lungs. As more and more pus is produced, the pus begins to push against the lungs making more difficult to breathe. The infection usually originates in the lungs and then spreads to the pleural space. A person usually has an underlying disease or infection before they develop pleural empyema including pneumonia, lung cancer, chest wound, surgery, or bone cancer.

Pus usually reaches a patient's pleural cavity from infection of the lung under it. This can be pneumonia, a lung abscess, or the pneumonitis that may follow an inhaled foreign body (usually in a child), or carcinoma of the bronchus (usually in a cigarette smoker). Pleural empyema often arises from an infection within the lung often associated with parapneumonic effusions where excess fluid accumulates in the pleural cavity. Occasionally, an empyema is tuberculous; rarely it may follow rupture of a liver or subphrenic abscess through the diaphragm.

FIG. 2 illustrates pleural empyema (e.g., pussy fluid with debris) within a pleural cavity. As shown, the pleural cavity 25a within pleura 20a surrounding lung 15a is normal and healthy without the presence of pleura empyema. However, pleural cavity 25b within pleura 20b surrounding lung 15b includes the presence of pleural empyema 50.

There are three stages: exudative, fibrinopurulent and organizing. In the exudative stage, the pus accumulates. This is followed by the fibrinopurulent stage in which there is loculation of the pleural fluid (the creation of pus pockets). In the final organizing stage, scarring of the pleural space may lead to lung entrapment. If the pus in his pleural cavity is left undrained, it will become too thick to flow down a long thin tube into a bottle. If the pus in his pleural cavity remains even longer it will be replaced by fibrous tissue which will be very difficult to remove.

Patients who contract pneumonia, for example, often develop pleural effusion and subsequent empyema. Once empyema sets in, peels and fibrinous tissue develop within the pleural cavity preventing full lung expansion aggravating pneumonia. The peel does not reabsorb and needs mechanical removal by surgical intervention. In order to remove the peel and fibrinous tissues, either open thoracotomy or thoracoscopic approach is used. The instruments used to retrieve the peel typically consist of graspers or ring forceps. These instruments are often inadequate and ineffective.

SUMMARY

Empyema removal devices are provided. The empyema removal devices remove empyema, including peels and fibrinous material, from a pleural cavity in a human or veterinary patient using minimally invasive insertion procedures. Also provided are systems and methods associated with the empyema removal devices that can be used in the treatment process to remove empyema from the pleural cavity of a patient.

BRIEF DESCRIPTION OF THE FIGURES

FIG. 6 illustrates a partial cutaway perspective view of an angled distal end of a pleural empyema removal device, according to certain embodiments;

FIGS. 7A-C illustrates exploded perspective views of removable distal ends of outer elongated members, according to certain embodiments;

FIG. 9A illustrates a side view of the distal end of a pleural empyema removal device prior to engagement of peel or fibrinous tissue associated with empyema, according to certain embodiments;

FIG. 9B illustrates a side view of the distal end of a pleural empyema removal device when device is pressed into the peel or fibrinous empyema, according to certain embodiments;

FIG. 9C illustrates a side view of the distal end of a pleural empyema removal device when penetrated peel or fibrinous empyema are suctioned within the opening of the hollow elongated member and cut by a movable blade, according to certain embodiments;

DETAILED DESCRIPTION

Devices

Figure 1:
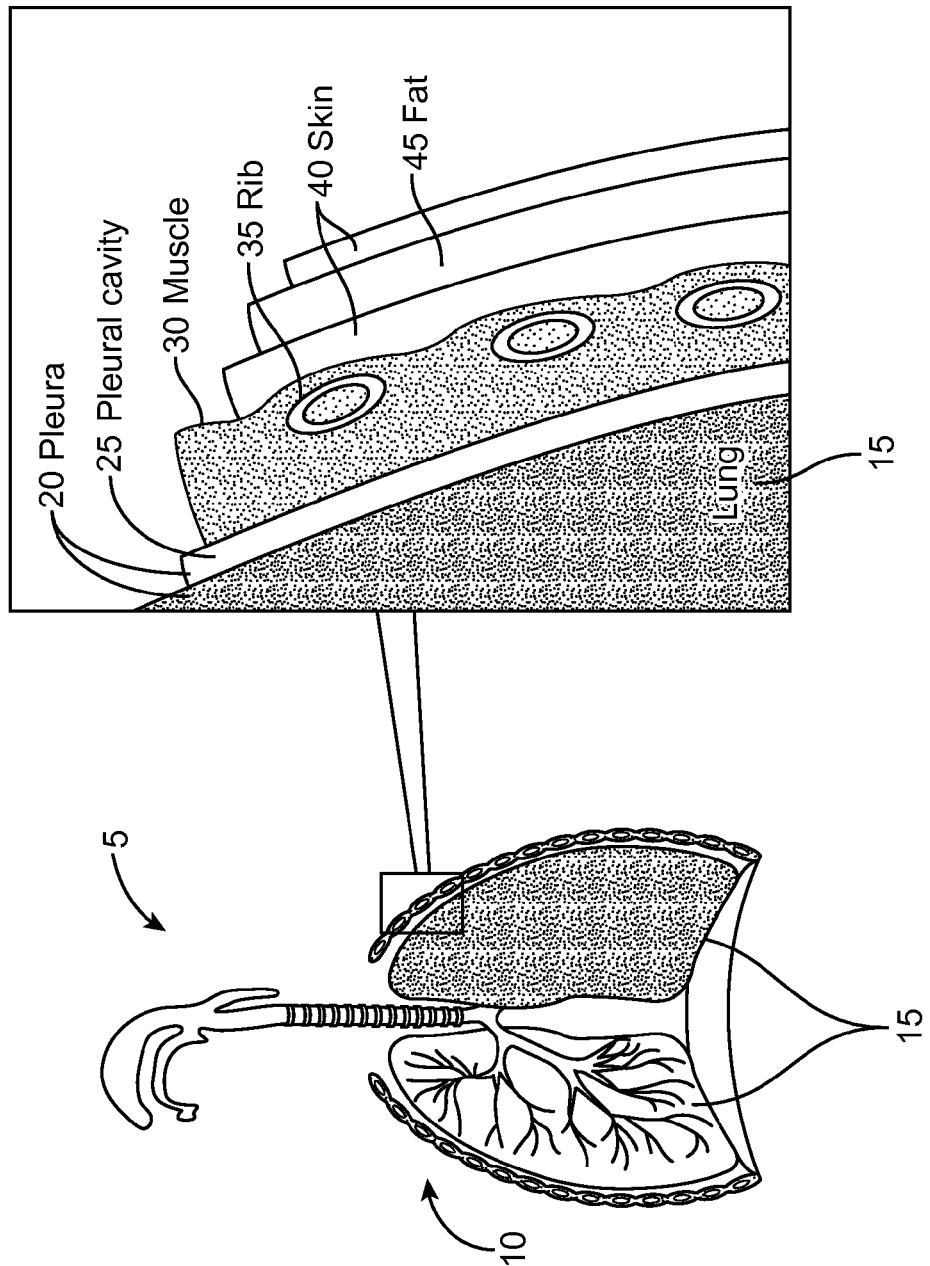
FIG. 1 illustrates a partial cutaway view of a human chest cavity.
Figure 2:
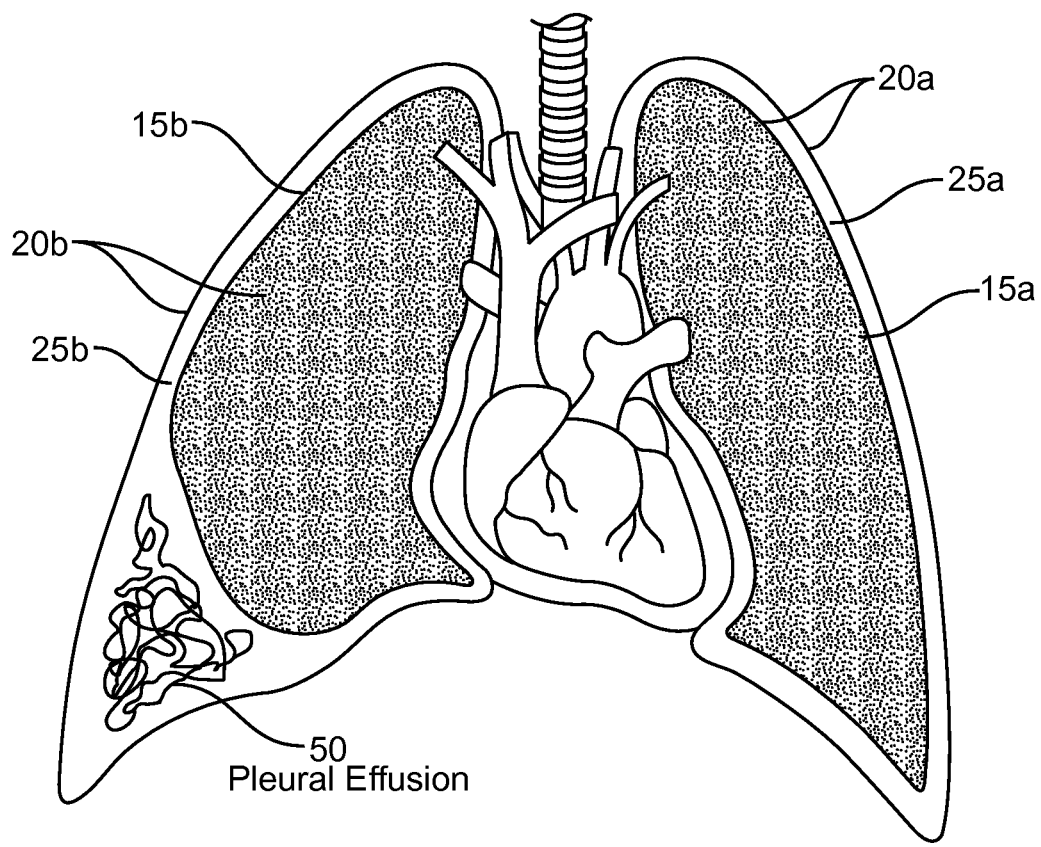
FIG. 2 illustrates pleural empyema within a pleural cavity of a human patient.

Aspects of the present disclosure include pleural empyema removal devices for removing empyema from a pleural cavity of a patient. The empyema removal devices are dimensioned such that at least the distal end of the devices can pass through a minimally invasive opening in the chest of a human or veterinary patient. The opening may be made by a minimal incision—e.g., 20 mm or less, such as 15 mm or less. Typically, the longest cross-sectional dimension of the distal end of the empyema removal device may be, for example, 20 mm or less, such as 15 mm to 3 mm. It should be appreciated that the empyema removal devices may also be used in larger openings within the chest cavity, however, smaller incisions enable quicker recovery, less associated pain, etc.

The term "distal end", as used herein, refers to the end of the device, component, member, etc., that is nearest to the pleural cavity of the patient during use. For example, the distal end of the empyema removal device is inserted into the pleural cavity. On the other hand, the term "proximal end", as used herein, refers to the end of the device, component, member, etc., that is farthest from the pleural cavity during use—e.g., nearer to the physician operating the device during the empyema removal procedure.

The devices include one or more elongated members that extend longitudinally. The length of the device should be long enough to insert the distal end of the device into the pleural cavity while maintaining a portion of the hollow elongated member outside the pleural cavity. The length of the device may range from, for example, 24 in. or less, such as 15 in. or less, including 12 in. or less.

In some aspects of the present disclosure, the pleural empyema removal device may be angulated to allow for easy access into the deep recess of the pleural cavity. It should be appreciated that any variety of angles—e.g., between 0 and 180 degrees—may be implemented as needed to access various target sites. In certain embodiments, the distal end of the empyema removal device is removable such that differently shaped distal ends may be removably coupled to the device. For example, in certain embodiments, the distal end of the outer elongated member may be removed to provide for variously shaped and angled distal ends.

Once inserted within the pleural cavity, the empyema removal devices are used to break and suction empyema out of the pleural cavity. For example, the devices may include a hollow elongated member that is coupled to a suction source that enables empyema to be suctioned within the hollow elongated member to a container or depository. The hollow elongated member includes an inner lumen and an opening at its distal end. The opening receives empyema, including peels and fibrinous tissues, which is suctioned into the hollow elongated member by a suction source applied from the proximal end of the hollow elongated member. In certain embodiments, the opening is at the tip of the distal end of the hollow elongated member. In other embodiments, the opening is on the side of the distal end of the hollow elongated member but not necessarily at the tip of the distal end. The hollow elongated member may be made from any variety of materials, including metals, metal alloys, polymers (e.g., plastics), etc. The diameter of the hollow elongated member may range from, for example, approximately 18 mm or less, such as 15 mm or less, including 5 mm or less.

In certain embodiments, the hollow elongated member includes a movable blade at its distal end to cut the empyema when moving. When activated, the movable blade may rotate, oscillate side to side, oscillate up and down, or otherwise be moved to facilitate cutting by the blade. The movable blade cuts the empyema to facilitate the suctioning of empyema within the inner lumen of the hollow elongated member without clogging (e.g., by cutting into smaller pieces).

Figure 5C:
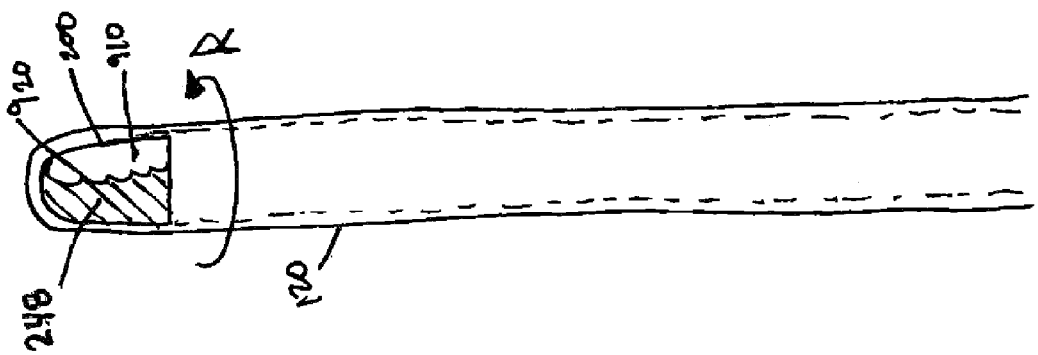
FIG. 5C illustrates a side view of the hollow elongated member and movable blade shown in FIG. 11B after the movable blade is rotated, according to certain embodiments.
Figure 5B:
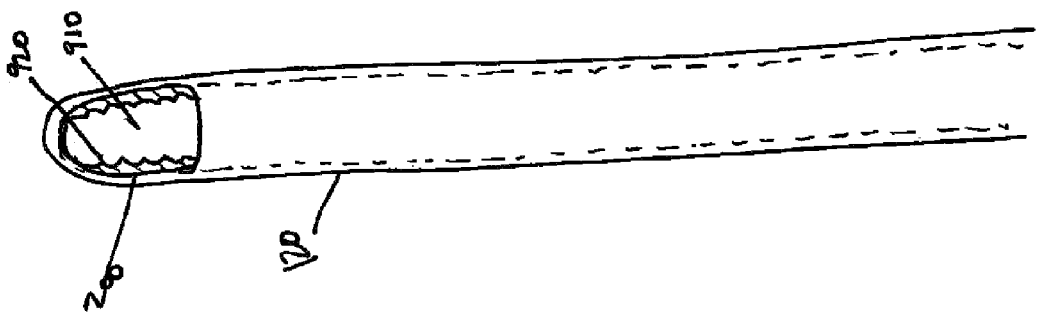
FIG. 5B illustrates a side view of the hollow elongated member and movable blade shown in FIG. 11A after assembled, according to certain embodiments.
Figure 5A:
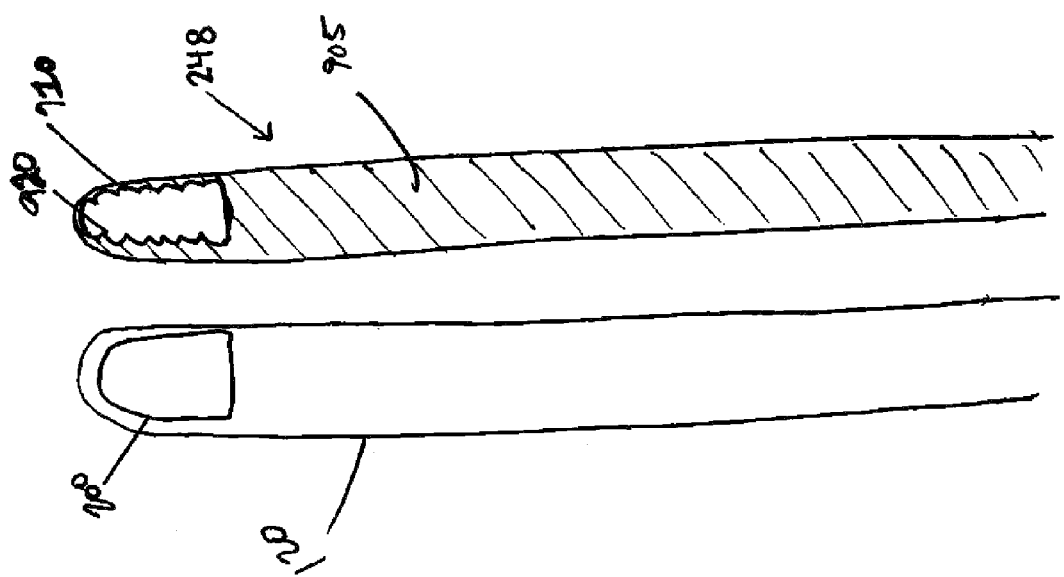
FIG. 5A illustrates a side view of a hollow elongated member and movable blade, according to certain embodiments.

The movable blade is disposed within the inner lumen of the hollow elongated member near the opening and distal end of the hollow elongated member. The movable blade decreases the likelihood that the opening or the inner lumen will become occluded by the empyema. While it is appreciated that in other embodiments the movable blade may be disposed anywhere between the opening and proximal end of the hollow elongated member, having the movable blade near the opening at the distal end decreases the chance of empyema becoming occluded within the inner lumen before reaching the movable blade. In some embodiments, the movable blade is a hollow member having an opening and serrated edge that is disposed within the hollow elongated member and rotates within the hollow elongated member, as shown in FIGS. 5A-C and discussed in further detail later.

It should be appreciated that the movable blade may be made from a variety of materials—e.g., metals, metal alloys, ceramics, polymers, etc. The term "movable blade" is used generally herein to refer to any element that may be moved sufficiently to cut through empyema, including peels and fibrinous tissues. It should be appreciated that the movable blade may include a sharp edge, however, a sharp edge is not necessarily required in all embodiments. Furthermore, it should be appreciated that the term "movable blade" is used generally herein and that more than one blade may be implemented. In certain embodiments, the movable blade is rotated in a plane transverse to the longitudinal axis of the hollow elongated member. In some embodiments, the movable blade is rotated about the longitudinal axis of the hollow elongated member.

In certain embodiments, a power source coupled to the proximal end of the hollow elongated member may be used to provide movement of the blade. For example, in some instances, an axis arm may extend within the inner lumen of the hollow elongated member, with a distal end of the axis arm coupled to the movable blade. Rotation of the axis arm by an actuating source such as a motor, for example, may rotate the axis arm and in turn rotate the blade. The actuating source may be any device that can be activated to provide movement to the movable blade. In certain embodiments, the actuating source may be disposed at the distal end of the hollow elongated member coupled to a conductive wire extending within the inner lumen of the hollow elongated member. Electrical power from a power source coupled to the distal end of the wire conductor and distal end of the device may be used to power the actuating source and move the blade. In certain embodiments, no motor is used and only the suction force provided by the source passing by the movable blade causes the blade to rotate. In certain embodiments, the movable blade comprises a hollow elongated member with an opening having serrated edges that is rotated by an actuating source coupled to the device.

In some aspects of the present disclosure, the pleural empyema removal devices include an outer elongated member that is disposed around the hollow elongated member. The outer elongated member includes an opening at its distal end. In certain embodiments, the hollow elongated member and the outer elongated member are cylindrical-shaped and coaxial such that they have a common longitudinal axis. In some instances, the outer elongated member is disposed around the hollow elongated member such that the hollow elongated member is abutting the inner surface of the outer elongated member so as to avoid empyema or other materials and fluids flowing between the two members.

The outer elongated member may be made from any variety of materials, including metals, metal alloys, polymers (e.g., plastics), etc. In certain embodiments, the outer elongated member is rigid to enable the device to be easily maneuvered within the pleural cavity of the patient. In other embodiments, the outer elongated member is semi-flexible. It should be appreciated that various combinations of rigidity and flexibility of the hollow elongated member and the outer elongated member may be implemented. For example, in certain embodiments, a rigid outer elongated member abuts a more flexible hollow elongated member, thus providing rigidity to the hollow elongated member. In other embodiments, both members are made from rigid materials—e.g., from the same materials, such as a metal or metal alloy, etc. In other embodiments, the outer elongated member may be a flexible material, such as tubing, that is disposed tightly around a rigid hollow elongated member.

In certain embodiments, the distal tip of the outer elongated member extends beyond the distal tip of the hollow elongated member and includes an opening at its distal tip. Therefore, the distal end of the hollow elongated member is within the outer elongated member. In this way, the outer elongated member contacts the target empyema before the hollow elongated member. Empyema may thus enter the outer elongated member through the opening at its distal end and continue to the opening of the distal end of the hollow elongated member. The distal end of the outer elongated member may serve to shield or prevent untargeted tissues from entering the opening of the hollow elongated member and being cut by the movable blade. The term "untargeted tissues" is used herein to refer to tissues that are not desired to be removed from the pleural cavity—e.g., pleura tissue, lung tissue, heart tissue, etc. Because such untargeted tissue that might be encountered is generally comprised of a surface (e.g., wall of the pleura, lung, or heart), such untargeted tissue may come in contact with the opening of the outer elongated member but will not extend far enough into the outer elongated member to reach the opening of the hollow elongated member and movable blade to become damaged. The distance between the tip of the distal end of the outer elongated member to the tip of the distal end of the hollow elongated member may range from, for example, 8 cm or less, including 4 cm or less, such as 2 cm or less. In some instances, the distance between the two tips may be 1 cm or less.

In some instances, the opening of the hollow elongated member may be implemented on the side of the distal end of the hollow elongated member to further reduce the chance of untargeted tissue from entering the opening of the hollow elongated member and becoming damaged. Empyema, on the other hand, may comprise thick fluid or gelatinous masses, and peels and fibrinous tissues, which are unlike surface walls of untargeted tissues and may otherwise enter the opening of the distal end of the outer elongated member and reach and enter the opening of the hollow elongated member. For instance, the distal end of the device may be pressed into empyema causing portions of the empyema to enter the opening at the distal end of the outer elongated member. However, the elasticity of the untargeted tissue is such that the distal end of the outer elongated member can contact the untargeted tissue without the untargeted tissue being pressed within the opening of the distal end of the outer elongated member.

Suction from a suction source may further assist pulling the empyema within the opening of the hollow elongated member. A surface wall of untargeted tissue, however, will not be suctioned within the opening. It should be appreciated that the suction force of the suction source should be strong enough to suction the empyema within the hollow elongated member but not so strong that it will damage a surface wall of untargeted tissue should it be suctioned against the opening of the distal end of the outer elongated member, sealing it shut. For example, in some instances, suction force of the suction source may range from 5 pounds per square inch (psi) to 60 psi, including 15 psi to 50 psi, such as 25 psi to 45 psi.

In certain embodiments, the opening of the distal end of the outer elongated member may include a pressure relief element to prevent a surface wall of untargeted tissue from sealing the opening shut. For example, the pressure relief element may be implemented as one or more notches or protrusions on the perimeter of the opening of the distal end of the outer elongated member, as shown in FIGS. 7A and 7B described herein later. Such notch or protrusion creates a gap between the surface wall of untargeted tissue and the perimeter of the opening, thus preventing the opening from being completely sealed by the surface wall of untargeted tissue and enabling air to escape pass. The distal end of the outer elongated member may be pressed into the empyema, on the other hand, allowing the entire opening to be covered by the empyema. The length of the notches or protrusions may range from, for example, 10 mm or less, including 5 mm or less, such as 3 mm or less.

The pressure relief element may be implemented in other various manners, such as various forms or shapes of the perimeter of the opening of the outer elongated member that prevent a surface wall of untargeted tissue from sealing the opening shut. For instance, the perimeter of the opening may not be flush, but rather include one portion of the perimeter that is distally distant from another portion of the perimeter, thus creating a step or gap between the two portions. For example, half of a circular perimeter of an opening may be distally distant from the other half of the circular perimeter, thus forming a "step" between the two halves. The "step" should be sufficiently long and steep to prevent the surface wall of the untargeted tissue to be suctioned flush against the step to be sealed shut. The length of the step may range from, for example, 10 mm or less, including 5 mm or less, such as 3 mm or less. The steepness of the "step" may in some instances be at an angle of 90 degrees. In some instances, the "step" portion of the perimeter may form an acute angle with one or both portions of the perimeter, as shown in FIGS. 8A and 8B described herein later.

In certain embodiments, the outer elongated member is flared at its distal end. The term "flared" is used herein to mean that the cross-sectional area is greater closer to the distal end. In some instances, for example when the outer elongated member is tubular or cylindrical-shaped, the flared distal end of the outer elongated member may be shaped like a frustum of a cone with a circular base. In such case, the wider base of the frustum would provide the opening at the distal end of the outer elongated member. The flared nature of the distal end facilitates the entry of empyema into the outer elongated member towards the distal end of the hollow elongated member. The flared nature of the distal end also enables a wider circumference, which enlarges the contact area for untargeted tissue and reduces the concentration of contact to a smaller area, thus reducing the potential of damage to the untargeted tissue when "poked" by the distal end. The diameter of the widest part of the outer elongated member may range from, for example, 20 mm or less, including 15 mm or less, such as 12 mm or less.

In certain embodiments, the outer elongated member includes one or more separating members extending across the opening of the distal end of the outer elongated member. The one or more separating members divide the opening into different sections. The separating members are used to penetrate empyema that passes through the opening of the distal end of the outer elongated member, resulting in separating, fragmenting, or otherwise cutting the empyema (e.g., into smaller pieces). Any clumping or chunks of empyema, for instance, will be reduced to facilitate suctioning within the inner lumen and to prevent clogging. For example, the separating members may comprise a thin piece of material of sufficient strength to penetrate through the empyema—e.g., metals, metal alloys, polymers (e.g., plastics), etc. The thickness of the separating member may range from, for example, 3 mm or less, such as 2 mm or less, including 1 mm or less.

When the distal end of the outer elongated member is pushed into masses of empyema, the empyema will be penetrated by the separating members, and thus less likely to become occluded within the outer elongated member, within the opening of the hollow elongated member, or within the inner lumen of the hollow elongated member.

The pattern and number of separating members may vary, as shown in FIGS. 9A-9D described herein later. It should be appreciated that as the sections of the opening become smaller and smaller, it becomes more difficult for thick empyema to be pass through the sectionalized opening.

When the distal end of the outer elongated member is pushed into empyema, the separating members press into the empyema eventually penetrating through the empyema as it passes by. However, because of the strength and elasticity, as well as surface wall nature of the untargeted tissue, the untargeted tissue is not pressed through the sections of the opening and cut by the separating member. Therefore, the one or more separating members provide further protection from damage to untargeted tissue.

In certain embodiments, the one or more separating members may extend distally from the perimeter of the opening of the outer elongated member. This reduces the likelihood that untargeted tissue may become flush with the opening and sealing it shut. The distally extending separating members form a structure that enable air gaps to exist between untargeted tissue and the opening of the outer elongated member, thus preventing the opening from being sealed shut by the untargeted tissue. The distally extending separating members may be pressed into the empyema causing the empyema to be penetrated as it passes the separating member to reach the opening of the outer elongated member. On the other hand, the surface wall of the untargeted tissue abuts the separating member but does not reach the opening of the outer elongated member, thus preventing damage to the untargeted tissue.

In certain embodiments, the one or more separating members may extend proximally from the perimeter of the opening—e.g., forming a concavity from the perimeter of the opening. In this way, the separating members protrude proximally inward and reduce the likelihood that the separating members may be damaged or contact untargeted tissues.

In certain embodiments, the hollow elongated member may include one or separating members that extend across the opening at its distal end—e.g., at the tip of the distal end. The above discussion regarding the separating members also applies here, and for the sake of clarity and brevity, these common features are not described in great detail again. In some instances, the device may include one or more separating members on both the opening of the outer elongated member and the opening of the hollow elongated member.

In some aspects of the present disclosure, the pleural empyema removal device includes a lighting element for lighting the pleural cavity near the distal end of the device. The lighting element may include any variety of lighting sources, such as light emitting diodes (LEDs), optical fibers with or without a lens, etc., that provides light to the pleural cavity. The lighting elements may be disposed within an additional hollow elongated member that extends adjacent to the outer elongated member, for example. For instance, an optical fiber may be extended along the inside of the additional elongated member, terminating at the distal end of the additional elongated member. The optical fiber provides light from a different location (e.g., a light source at the proximal end of the device) to the pleural cavity. In other embodiments, a LED may be disposed at the distal end of the device (e.g., distal end of the additional elongated member) with a conductive wire extending within the additional elongated member to a power source at the proximal end of the device.

In certain embodiments, a visualization element such as a camera or lens may be disposed at the distal end of the additional elongated member to enable photographic and/or video images to be displayed on a monitor, printer, etc. For example, in some instances, a lens may be positioned at the distal end of the additional elongated member to guide light to a camera that is coupled to the proximal end of the device. It should be appreciated that any variety of image producing technologies may be implemented—e.g., any video imaging technology used with fiberscopes or fiber optic cameras. For instance, the fiber optic camera may comprise an optical fiber extending within the additional elongated member, a lens at the distal end of the optical fiber, and a camera at the proximal end of the optical fiber that displays images of light received via the lens and optical fiber. In other embodiments, a camera (or any image producing device, such as a photodetector, etc.) may be disposed in the additional elongated member (e.g., at the distal end of the additional elongated member) and electrically coupled to a monitor via an electrical wire extending along or within the outer elongated member.

Having a visualization element and lighting element as part of the empyema removal device and disposed at the distal end of the device can provide several advantages, such as eliminating the need for an additional port within the chest cavity for a separate camera device, and eliminating the need to coordinate a separate camera device from the removal device by providing the viewing area near the distal end of the device. Furthermore, suction from the device also removes the CO2 thereby collapsing the cavity and making visualization difficult. Thus, the light source assists in improving visualization at the targeted area.

As stated above, in certain embodiments, a second hollow elongated member is coupled along the outside of the outer elongated member to house visualization elements and/or lighting elements, or components thereof. For example, the conductive wire or the optical fiber may extend within the second hollow elongated member that is coupled along side the outer elongated member. Any variety of coupling techniques may be implemented to couple the two members—e.g., snap together, tied together, clipped together, bolted together, soldered together, welded, etc. In some instances, the two members may be removably coupled to one another such that the two members may be separated when desired—e.g., when the device is not in use. In other embodiments, the two members may be attached or formed by one unitary piece of material.

The second hollow elongated member may include a coupling element at its proximal end that couples the device to additional devices—e.g., a monitor, electrical or light source, etc. For instance, the coupling element may comprise an input jack or port, or other form of connector, which receives the appropriate cable for connection to the additional device.

In some aspects of the present disclosure, gas is delivered to inflate the pleural cavity. While in some instances the lung may be collapsed by the physician to provide more space for the empyema removal procedure, the suction from the device can cause the pleural cavity to collapse upon the lung, inhibiting the maneuvering of the device and impairing the visualization of the pleural cavity. The introduction of gas, such as carbon dioxide (CO2), for example, may help alleviate or prevent the collapsing of the pleural cavity.

In certain embodiments, the empyema removal device includes a delivery member that is used to deliver gas to the pleural cavity. The term "delivery member" is also a hollow elongated member, but is used for the delivery of gas. For example, the delivery member may be disposed adjacent to the outer elongated member.

In certain embodiments, the delivery member is implemented as an additional hollow elongated member that is coupled to, and extending along, the outside the outer elongated member. The distal end of the delivery member may be positioned at the distal end of the outer elongated member (e.g., at the distal tip or near the distal tip) such that gas may be delivered to the pleural cavity from the distal end of the device. The proximal end of the delivery member is coupled to a coupling element on the proximal end of the device that is used to couple the delivery member to a gas source.

Any variety of coupling techniques may be implemented to couple the two members—e.g., snap together, tied together, clipped together, bolted together, soldered together, welded, etc. In some instances, the two members may be removably coupled to one another such that the two members may be separated when desired—e.g., when the device is not in use. In other embodiments, the two members may be attached or formed by one unitary piece of material.

As stated above, the empyema removal devices may be coupled to various devices such as a suction source, lighting or power source, camera source, gas source, actuating source, etc. In certain embodiments, the empyema removal devices include coupling elements at the proximal end of the device. It should be appreciated that the coupling elements may be located anywhere on the device that remains outside the chest cavity of the patient, and thus is not required to be at the tip of the proximal end of the device. It should be appreciated any variety of coupling mechanisms may be implemented—e.g., male/female adaptors, threaded connections, BNC connections, etc.

For example, a coupling element may be disposed on the empyema removal device to couple a suction source to the hollow elongated member. A coupling element may be disposed on the empyema removal device to couple an actuating source to the movable blade. A coupling element may be disposed on the empyema removal device to couple a gas source to the delivery member. A coupling element may be disposed on the empyema removal device to couple a monitor, or other viewing device, to the device. Further, a coupling element may be disposed on the empyema removal device to couple a lighting source, camera source, or power source for a lighting element or visualization element. It should be appreciated that one or more coupling elements may provide coupling for one or more devices. Furthermore, it should be appreciated that the functionality of multiple devices may be provided by a single device. Still further, it should be appreciated that various connectors, cables, wires, etc., may be used between the coupling element and the corresponding source.

In use, the distal end of the empyema removal device is inserted within a pleural cavity of a human or veterinary patient—e.g., via a minimally sized incision on the chest cavity. In some instances, the lung associated with the target pleural cavity may be deflated to provide additional space for the procedure. As, the distal end of the outer elongated member enters the pleural cavity, the lighting element and visualization element enable the necessary light and video images for the physician to see within the pleural cavity. The lighting element and visualization element should provide viewing area of at least the immediate area in front of the distal end of the outer elongated member so that the operator may know what is in the area immediately in front of the distal end of the device. In some instances, a wider viewing area may be implemented (e.g., with a wide-angle lens) so that the operator may see what is to the right and left peripherals of the distal end of the outer elongated member. Gas is delivered via the delivery member to inflate the pleural cavity to maintain space within the pleural cavity for viewing and maneuvering.

The operator maneuvers the device while viewing within the pleural cavity on the monitor. The operator may then move the distal end of the outer elongated member towards any identified empyema. Suction provided by the suction source via the proximal end of the hollow elongated member enables empyema within the opening of the distal end of the outer elongated member to be suctioned towards the opening of the hollow elongated member. In certain embodiments, the suction source provides continuous suction to the hollow elongated member. In certain embodiments, the operation may freely control the activation and deactivation of the suction (e.g., by a trigger, switch, or other activation element) so that operation may be more selective about what is being suctioned into the device.

As the operator presses the distal end of the outer elongated member into thicker empyema, such as peels and fibrinous tissues, the separating members disposed across the opening of the outer elongated member penetrate the empyema, fragmenting the empyema. Suction may also assist in the pulling the empyema through the opening while penetrated by the separating members. The empyema is then suctioned towards and into the opening of the hollow elongated member. When the empyema enters the opening of the hollow elongated member, it is further cut by the movable blade (e.g., rotating blade, oscillating blade, etc.). The speed and configuration of the blade may vary and may affect the size and consistency of the empyema that has been cut by the blade. The empyema is then suctioned along the inside of the hollow elongated member to the proximal end of the hollow elongated member. The empyema that exits the proximal end of the hollow elongated member is deposited into a depository—e.g., within the suction source.

Figure 3A:
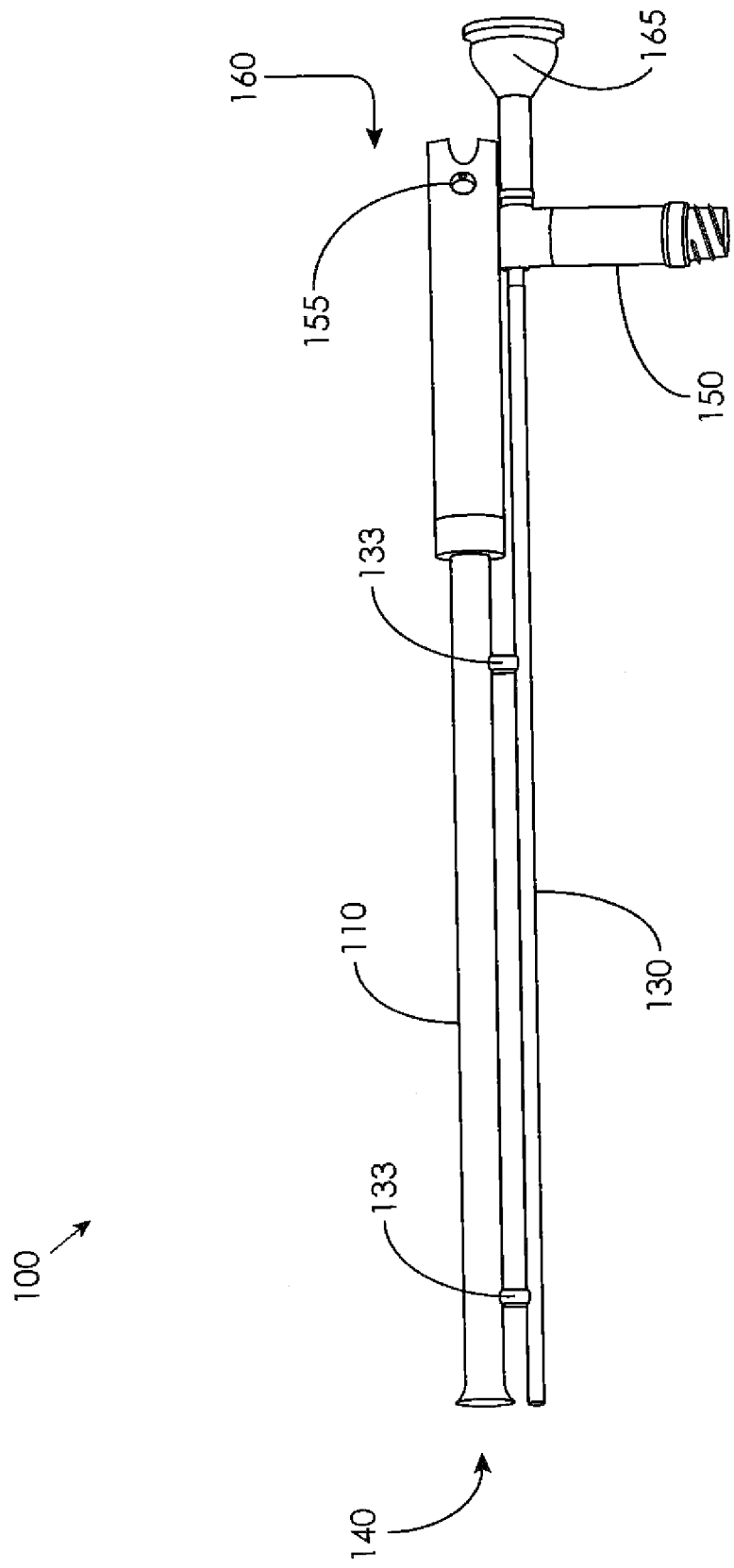
FIG. 3A illustrates a side view of a pleural empyema removal device, according to certain embodiments.
Figure 3B:
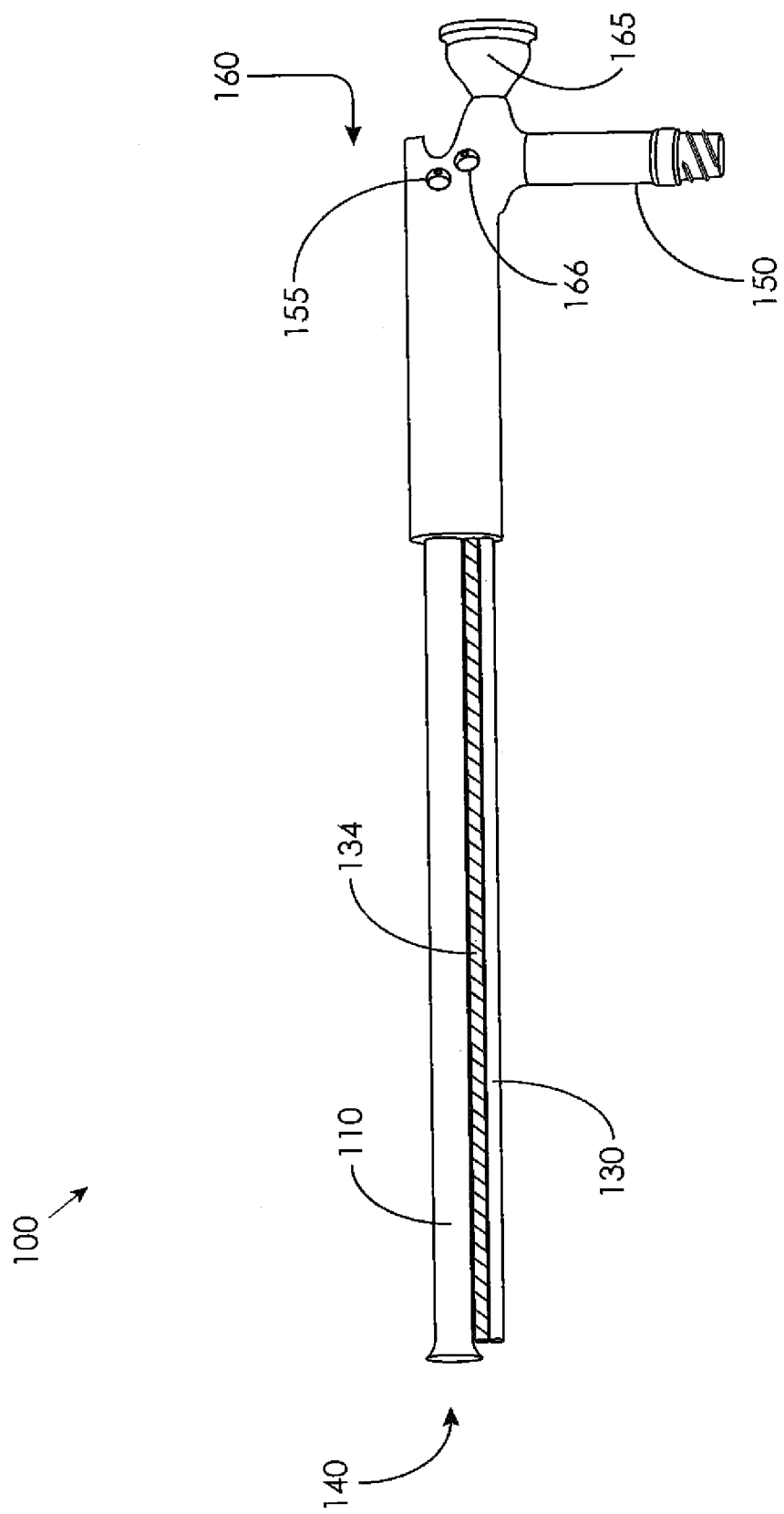
FIG. 3B illustrates a side view of a pleural empyema removal device, according to certain embodiments.

FIGS. 3A and 3B illustrate a side view of empyema removal devices, according to certain embodiments. Empyema removal device 100 includes outer elongated member 110 which surrounds hollow elongated member (not shown in FIG. 3). Distal end 140 and proximal end 160 of device 100 is shown for reference purposes.

Device 100 also includes coupling element 155 which is used to couple the device 100 to a suction source (not shown). The suction source is coupled to the coupling element 155 and provides suction to the hollow elongated member (not shown) that is disposed within the outer elongated member 110. In the embodiment shown, coupling element 155 is also used to couple the device to an actuating source for moving the movable blade. It should b appreciated that in other embodiments, the actuating source and suction source may couple to separate coupling elements on the device.

Device 100 also includes an additional elongated member 130 that houses components for lighting and/or visualization. In some aspects, elongated member 130 is used to provide light to the distal end of the device. Any variety of techniques may be implemented to provide light. In certain embodiments, elongated member comprises an optical channel (e.g., optical fiber) and/or optical lens to carry light to the distal end of the device and provide light to the pleural cavity. For example, a lighting source may be coupled to the coupling element 150 and provide light that is transmitted down the optical channel to the distal end of the elongated member 130. In other embodiments, a small light source may be included at the distal end of elongated member 130 to provide light to the pleural cavity. In such case, the coupling element 150 may be coupled to a power source that provides electrical power to the light source.

In some aspects, elongated member 130 is used to enable viewing within the pleural cavity at the target site. For example, viewing lens 165 is disposed at the proximal end of the elongated member to enable the user to visualize within the pleural cavity. In some instances, a camera or other image producing device may be coupled to the viewing lens 165 to provide still images and/or video images of the pleural cavity. The camera device receives light from the lens and converts it into images or signals representative of images within the pleural cavity for display on a monitor, for example. In other embodiments, a small camera or image producing device is implemented at the distal end of elongated member 130.

In some aspects of the present disclosure, the elongated member 130 provides lighting and/or visualization to an area that is not necessarily directly in front of the device. For example, in some instances, the distal end of the elongated member may include a wide-angle lens to enable a broader viewing angle. In other instances, the distal end of the elongated member may be angled. In certain embodiments, the distal end of the elongated member is removably coupled such that different types of distal ends may be coupled to provide different types of viewing features.

In FIG. 3A, elongated member 130 is shown connected to outer elongated member 110 by spacers 133 that are disposed between both members 110 and 130. It should be appreciated that elongated member 130 may be coupled to outer elongated member 110 in various manners—e.g., welded, tied together, hooked, hinged, clamped, snap-fit together, fastened together, etc. It should also be appreciated that elongated member 130 and outer elongated member 110 may not be spaced apart in other embodiments, but rather abutting one another.

In certain embodiments, device 100 includes a delivery member which delivers gas (e.g., carbon dioxide) to the pleural cavity. In FIG. 3B, elongated member 130 is shown coupled to the outer elongated member 110 via a delivery member 134 adjacent to the outer elongated member 110. Device 100 is shown including coupling element 166 which is used to couple the device 100 to a gas source (not shown). For example, coupling element 166 may be coupled to a carbon dioxide gas source and provide carbon dioxide to delivery member 134. The carbon dioxide is carried within the delivery member 134 and expelled out the distal end of the delivery member 134. It should be appreciated that the configuration of the elongated member 130, outer elongated member 110, and delivery member 134 may vary. For example, the elongated member 130 and delivery member 134 may each abut the outer elongated member 110—e.g., on opposite sides of the outer elongated member 110, adjacent one another, etc. Moreover, it should be appreciated that the delivery member may be coupled to outer elongated member 110 in various manner—e.g., welded, tied together, hooked, hinged, clamped, snap-fit together, fastened together, etc. Delivery member 134 is shown cross-hatched in FIG. 3B to assist in distinguishing it from elongated members 110 and 130. Delivery member 134 may be made of any variety of materials, such as those described for elongated members 110 and 130. It should be appreciated that delivery member 134 and elongated members 110 and 130 may all be the same material in some embodiments, and different materials in other embodiments. Moreover, each of the members 110, 130, and 134 may be made from a rigid or flexible material.

Figure 4:
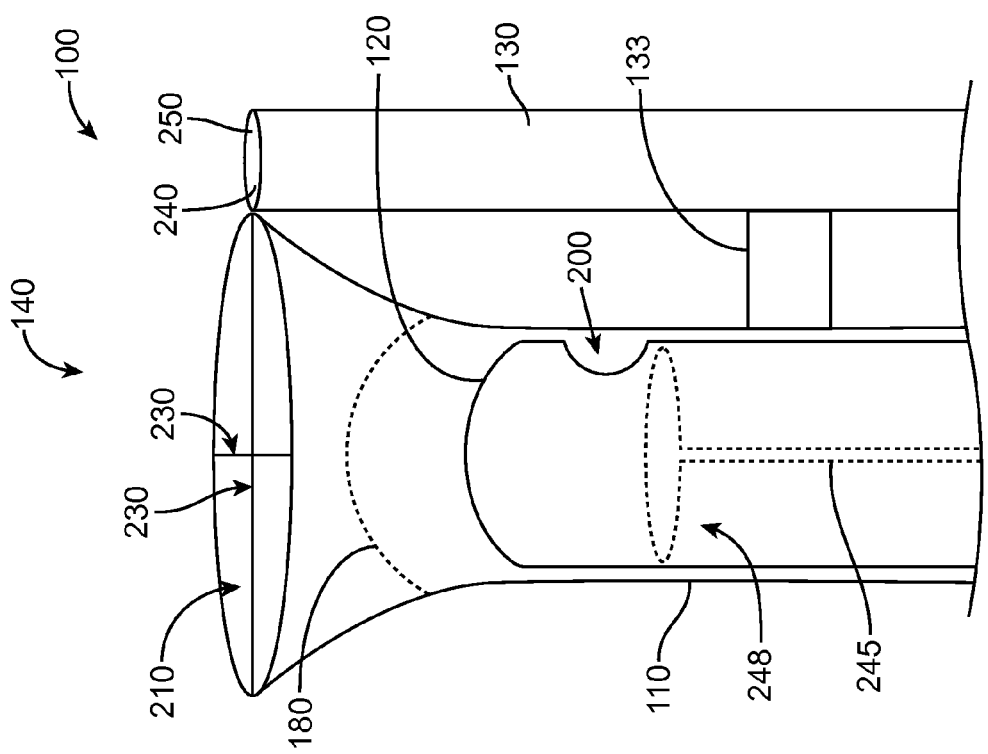
FIG. 4 illustrates a partial cutaway view of the distal end of the pleural empyema removal device, according to certain embodiments.

FIG. 4 illustrates a partial cutaway view of the distal end of the pleural empyema removal device, according to certain embodiments. As shown, the pleural empyema removal device 100 includes a flared outer elongated member 110 and a hollow elongated member 120 within the outer elongated member 110. Distal end 140 is shown for reference purposes. The cutaway boundary for the partial cutaway view is represented by dotted line 180. Thus it is illustrated that the hollow elongated member 120 is within the outer elongated member 110. In the embodiment shown, the outer elongated member 110 is abutting the hollow elongated member 120 so that air and fluid cannot pass between the two elongated members. In this way, all of the suction force provided at the proximal end of the hollow elongated member 120 is provided at the opening 200 of the hollow elongated member 120 as well as at the opening 210 of the outer elongated member 110. Opening 200 is located on the side of the hollow elongated member 120 at its distal end. The suction source (not shown) is coupled to the proximal end of the device 100.

Separating members 230 are shown disposed across the opening 210 of the outer elongated member 110. As described above, the separating members 230 penetrates empyema passing through the opening 210. After the empyema is penetrated by the separating member 230, it continues to be suctioned within the opening 200 of the hollow elongated member 120 and then further cut by movable blade 248 to further facilitate suctioning and prevent clogging. Movable blade 248 is connected to axis arm 245 that extends along the inside of the hollow elongated member 120. An actuating source (not shown), such as a motor, coupled to the proximal end of the device 100 provides the necessary power to rotate blade 248 within the hollow elongated member 120.

Looking ahead, FIGS. 5A-5C illustrates an example movable blade configuration, according to certain embodiments.

FIG. 5A illustrates a side view of a hollow elongated member and movable blade disassembled, according to certain embodiments. Furthermore, FIG. 5B illustrates a side view of the hollow elongated member and movable blade shown in FIG. 5A after assembled, according to certain embodiments. FIG. 5C illustrates a side view of the hollow elongated member and movable blade shown in FIG. 5B after the movable blade is rotated, according to certain embodiments.

As shown in FIGS. 5A-C, hollow elongated member 120 includes an opening 120 at the distal end. The opening 200 is an opening that provides entry into the hollow elongated member 120 (e.g., as shown in FIG. 4). Movable blade 248 comprises a second hollow elongated member 905 having an opening 910 at the distal end. The opening 910 is disposed on the second hollow elongated member 905 to properly align with opening 200 when assembled. Opening 910 is shown having serrated edges 920 surrounding its perimeter. Movable blade 248 is illustrated with cross-hatched diagonal lines to facilitate understanding of the figures.

When assembled, movable blade 248 is disposed within hollow elongated member 120, as shown in FIG. 5B. The movable blade 248 is sized slightly smaller than the hollow elongated member 120 and permitted to rotate within hollow elongated member 120, as shown in FIG. 5C. When the movable blade 248 is rotated within hollow elongated member 120 (e.g., as represented by direction arrow R shown in FIG. 5C), the opening 910 and serrated edge 920 of the movable blade 248 are repeatedly rotated past opening 200 of hollow elongated member 120. As opening 910 overlaps with opening 200, empyema is suctioned into the openings 120 and 910. As the serrated edge 920 rotates across opening 200, the empyema is cut by the serrated edge 920. It should be appreciated that in other embodiments the edge of the opening 910 may not necessarily be serrated but sufficiently sharp to cut through empyema when rotated across the opening 200. In other embodiments, opening 200 is serrated or sufficiently sharp to cut through empyema when rotated across serrated or non-serrated opening 910.

Returning to FIG. 4, device 100 also includes an additional elongated member 130 that is attached along the outside of the outer elongated member 110. Optical fiber 240 is disposed within the additional elongated member 130 coupled to spacers 133. Optical fiber 240 carries light from a light source coupled to the proximal end of device 100 and emits the light out of the distal end of the optical fiber and into the pleural cavity. Lens 250 is disposed at the distal end of the additional elongated member 130. Light received by the lens travels down the optical fiber and is received by a camera device that is coupled to the proximal end of the device (e.g., a viewing lens). The camera device may be coupled to a monitor, or other viewing device, to enable still images and/or video images to be displayed and viewed by the operator. In other embodiments, one or more wire conductors may be disposed within the length of the additional elongated member 130 to provide electrical power necessary to power an LED and/or camera disposed at the distal end of the elongated member 130.

FIG. 6 illustrates a partial cutaway perspective view of an angled distal end of a pleural empyema removal device, according to certain embodiments. The device 100 shown is similar to the device shown in FIG. 4 except that the flared distal end of outer elongated member 110 is angled. In the embodiment shown, additional elongated member 130 is also angled. In other embodiments, additional elongated member 130 is straight but includes a lens that enables viewing in the direction of the angled outer elongated member 110. For example, additional elongated member 130 may include a wide angle lens and/or a lens directed in the direction of the angled outer elongated member 110.

In some aspects of the present disclosure, the distal end of the outer elongated member is removable. FIGS. 7A-C illustrates exploded perspective views of removable distal ends of outer elongated members, according to certain embodiments. As shown, outer elongated member 110 includes a removable distal end 960 that couple to one another at ends 940 and 950. Ends 940 and 950 may mate with one another in any variety of manners—e.g., screw, snap, clasp, clamp, fasten, etc. In FIG. 7A, the removable distal end 960 is not angled. In FIGS. 7B and 7C, the removable distal end 960 are angled. In some embodiments, the removable distal end are radiopaque and thus may be located or detected using X-rays or other forms of radiation to prevent the device from being left in the body. It should be appreciated that other elements of the pleural empyema removal device may also be radiopaque.

Figure 8:
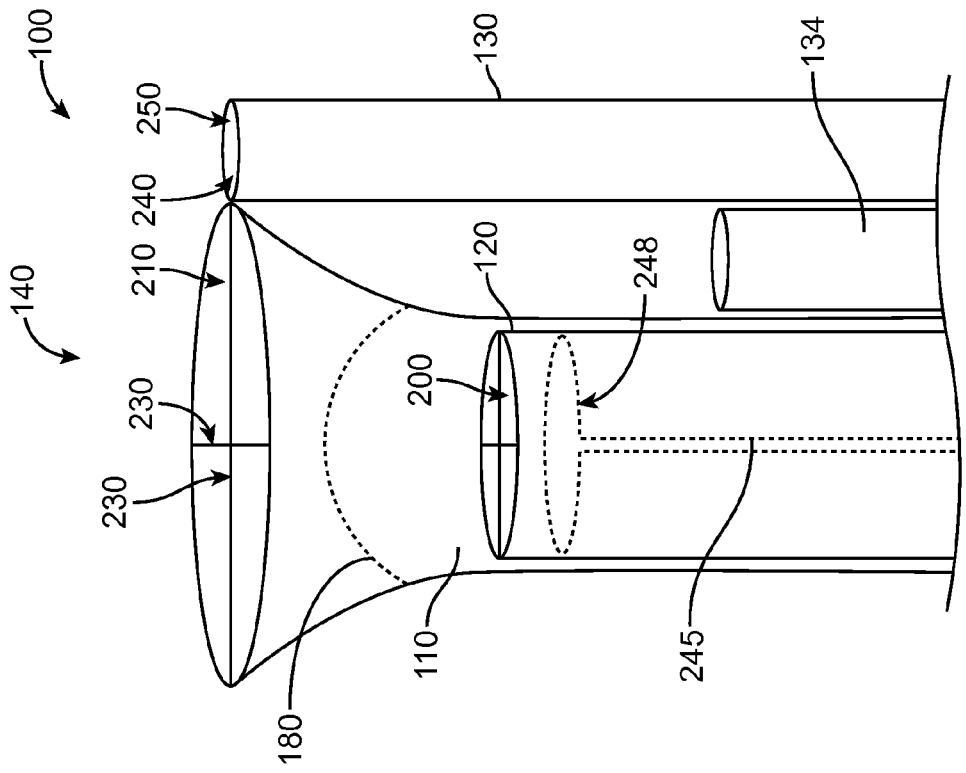
FIG. 8 illustrates a partial cutaway view of the distal end of the pleural empyema removal device, according to certain embodiments.

FIG. 8 illustrates a partial cutaway view of the distal end of an empyema removal device, according to certain embodiments. The empyema removal device 100 and its elements are similar to those shown in FIG. 4 except that the device 100 shown in FIG. 8 includes an opening 200 at the tip of the distal end of the hollow elongated member 120, and also includes separating members 235 across the opening 200 of the hollow elongated member 120. The separating members 235 function similar to the separating members 230 of the outer elongated member 110 and further penetrate any empyema passing through opening 200. FIG. 8 also differs by including a delivery member 134 that provides gas such as carbon dioxide to the pleural cavity. Delivery member 134 is implemented as a hollow elongated member disposed adjacent the outer elongated member 110 and additional elongated member 130. The proximal end of the delivery member 134 is coupled to a gas source via a coupling element (not shown) at the proximal end of the delivery member 134.

FIGS. 9A, 9B, and 9C illustrate side views of the distal end of an empyema removal device at different times during the empyema removal process, according to certain embodiments. FIG. 9A illustrates a side view of the distal end of an empyema removal device 100 prior to engagement of peel or fibrinous empyema 300. The distal end 140 of the outer elongated member 110 includes opening 210 and separating members 230 disposed across the opening 210. Additional elongated member 130 includes optical fiber 240 and lens 250 at its distal end that enables visualization of the pleural cavity by the operator. Using video enabled by the lens 250 and optical fiber 240, the operator may maneuver and advance the distal end of the device 100 towards the target empyema 300. Carbon dioxide gas is provided within the pleural cavity by delivery member 134 as needed to keep the pleural cavity inflated. FIG. 9B illustrates a side view of the distal end of an empyema removal device 100 when device is pressed into the peel or fibrinous empyema 300. As the distal end of the device 100 is advanced into the target empyema 300, the distal end of the outer elongated member 110 presses into the target empyema 300. The target empyema 300 is penetrated by the separating members 230 across the opening 210, resulting in smaller pieces 310 of empyema. The smaller pieces 310 are suctioned towards the opening 200 of the hollow elongated member 120. The distal end of the outer elongated member 110 is also contacts the untargeted tissue 305 but does not damage the untargeted tissue. The untargeted tissue may elastically deform but does not enter the outer elongated member 110 or get cut by the separating members 230. FIG. 9C illustrates a side view of the distal end of a pleural empyema removal device when penetrated peel or fibrinous empyema are suctioned within the opening of the hollow elongated member 120 and cut by movable blade 248 (not shown in FIGS. 9A-C) that is being rotated by a motor (not shown) coupled to the proximal end of device 100.

Figure 10A:
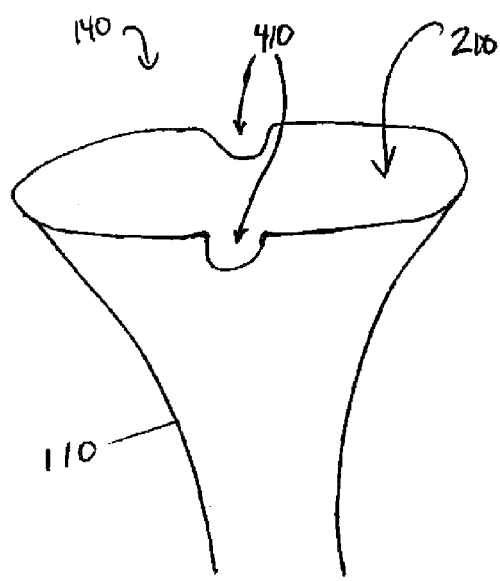
FIG. 10A illustrates a distal end of an outer elongated member having an opening with notches, according to certain embodiments.
Figure 10B:
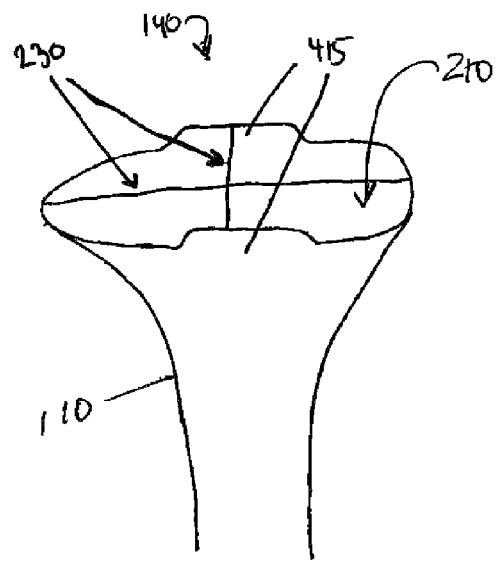
FIG. 10B illustrates a distal end of an outer elongated member having an opening with protrusions, according to certain embodiments.

FIGS. 10A and 10B illustrate a distal end of an outer elongated member having an opening with notches and protrusions respectively, according to certain embodiments. As shown, outer elongated member 110 includes opening 210 at a distal end 140. In FIG. 10A, the perimeter of opening 210 includes notches 410. It should be appreciated that while only two notches are shown, any number of notches may be implemented. In FIG. 10B, the perimeter of opening 210 includes protrusions 415. It should be appreciated that while only two protrusions are shown, any number of protrusions may be implemented. Furthermore, it should be appreciated that the notches and protrusions may be implemented in conjunction with separating members 230, as shown in FIG. 10B with separating members 230.

Figure 11A:
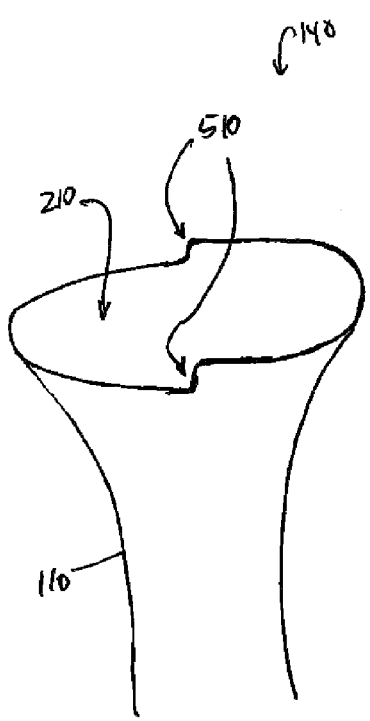
FIG. 11A illustrates a distal end of an outer elongated member that includes an opening having one portion of its perimeter that is distally distant from another portion of its perimeter, according to certain embodiments.
Figure 11B:
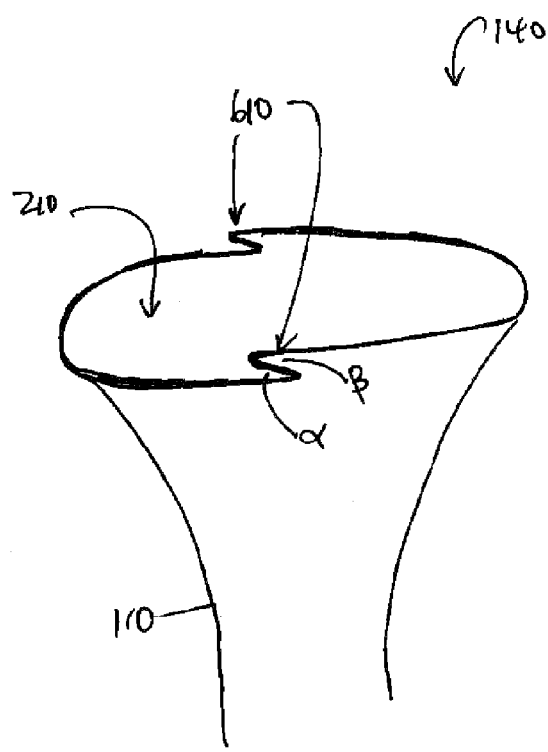
FIG. 11B illustrates a distal end of an outer elongated member that includes an opening having one portion of its perimeter that is distally distant from another portion of its perimeter, according to certain embodiments.

FIGS. 11A and 11B illustrate a distal end of an outer elongated member that includes an opening having one portion of its perimeter that is distally distant from another portion of its perimeter, according to certain embodiments. As shown, outer elongated member 110 includes opening 210. In FIG. 11A, the perimeter of opening 210 includes steps 510 that make one portion of the perimeter distally distant from the other portion of the perimeter. Steps 510 provide an uneven surface that makes it more difficult for untargeted tissue from becoming flush against the opening to seal it shut. In FIG. 11B, steps 610 form acute angles with the portions of the perimeter of the opening 210.

Figure 12A:
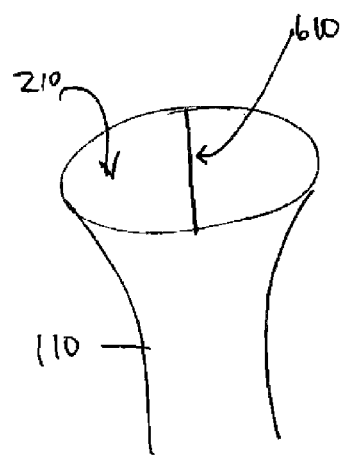
FIGS. 12A-12D illustrates various configurations of separating members across the opening of the distal end of the outer elongated member, according to certain embodiments.
Figure 12B:
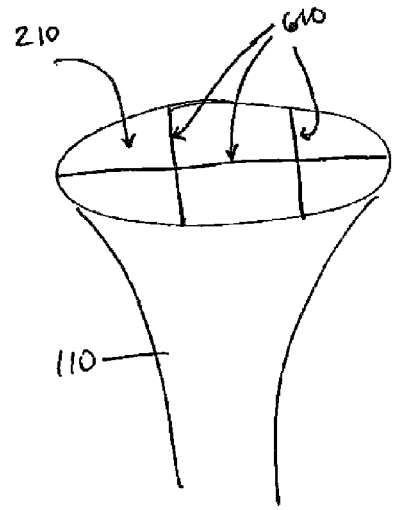
Figure 12C:
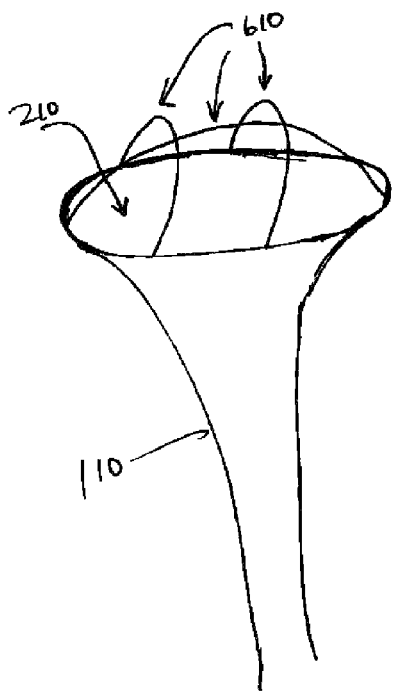
Figure 12D:
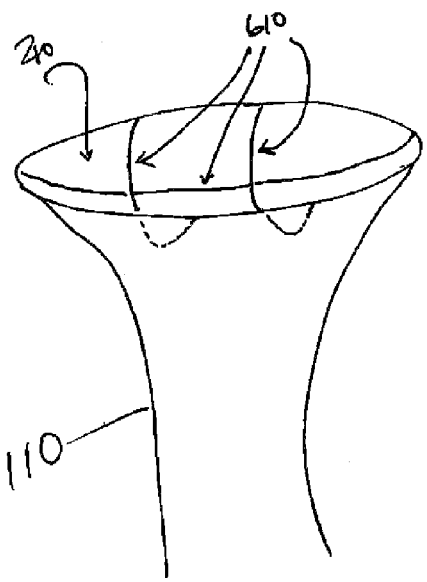

FIGS. 12A-12D illustrates various number and configurations of separating members across the opening of the distal end of the outer elongated member, according to certain embodiments. It should be appreciated that these embodiments are exemplary and that other configurations are possible. As shown, outer elongated member 110 includes opening 210 and separating members 610 extending across the opening 210. In FIG. 12A, one separating member 610 is disposed across the center of a circular opening 210, sectionalizing the opening into two semi-circular sections. In FIG. 12B, three separating members 610 extend across the circular opening 210 such that one separating member is perpendicular to two parallel separating members. The opening 210 is thus sectionalized into six sections. In FIG. 12C, the three separating members 610 protrude distally outward from the opening 210. The protruding separating members may reduce the likelihood that untargeted tissue may become flush with the opening 210 and sealing it shut. It should be appreciated that the separating members 610 may also be implemented in conjunction with the notches and protrusions described above. In FIG. 12D, the three separating members 610 protrude proximally inward and reduce the likelihood that the separating members 610 may be damaged or contact untargeted tissues.

Methods

In some aspects of the present disclosure, methods of removing empyema from a pleural cavity of a human or veterinary patient using an empyema removal device, such as the one described above, are provided.

In certain embodiments, the methods include inserting a distal end of the empyema removal device into a pleural cavity of the patient. For example, in some instances, an incision may be formed in the chest cavity of the patient and the distal end of the empyema removal device inserted into the incision to access the pleural cavity. The incision may be formed by a physician, for example, who may also be the operator of the empyema removal device. The methods include advancing the distal end of the empyema removal device towards target empyema, which may include peels or fibrinous tissues, within the pleural cavity. The operator may then move the distal end of the outer elongated member towards any identified empyema. The methods include providing suction from a suction source at the proximal end of the device. For example, the suction source may be coupled to the proximal end of the hollow elongated member to provide suction within the hollow elongated member and at the end of the device. Suction provided by the suction source enables empyema within the opening of the distal end of the outer elongated member to be suctioned towards the opening of the hollow elongated member. The suction source may be an external device that is coupled to the device via a connection line or hose, for example.

In certain embodiments, the suction source provides continuous suction to the hollow elongated member. In other embodiments, the operation may freely control the activation and deactivation of the suction (e.g., by a trigger, switch, etc.) so that operation may be more selective as to when suction is applied and as to what is being suctioned into the device.

In certain embodiments, the methods may include displaying the pleural cavity on one or more monitors or other viewing devices. In such case, the operator may maneuver the device while viewing within the pleural cavity on a monitor. For example, the empyema removal device may include a visualization element (e.g., camera or lens) at its distal end that enables video or still images of the pleural cavity to be provided on the monitor. For example, the visualization element may comprise a lens that enables received light to be transmitted along an optical fiber to an image sensor device which converts the received light into electrical signals for display on the monitor.

In certain embodiments, the methods include emitting light from a lighting element disposed at a distal end of the empyema removal device—e.g., a light emitting diode or other light emitting device. In some instances, the lighting element may comprise an optical fiber that terminates at the distal end of the device. The optical fiber receives light within its proximal end—e.g., from a light source at a proximal location, such as on the proximal end of the device or from a remote location that is coupled to the device (e.g., via an optical cable). The emitted light from the lighting element provides the necessary light for the visualization element. Having the lighting element and the visualization element at the distal end of the device reduces the number of ports necessary for the empyema removal procedure. In other embodiments, for example, a lighting device and/or visualization device (e.g., a camera) may be inserted into a separate port in the chest cavity than the empyema removal device.

In certain embodiments, the methods include penetrating empyema with separating members as it enters the opening at the distal end of the device. For example, separating members may be disposed across the opening of the outer elongated member to penetrate the empyema entering the opening. Suction may also assist the separating members in penetrating the empyema by pulling the empyema past the separating members. The empyema is then suctioned towards and into the opening of the hollow elongated member. The empyema is then suctioned along the hollow elongated member into a depository—e.g., contained within the suctions source.

In certain embodiments, the methods include cutting the empyema by a movable blade—e.g., rotating blade, oscillating blade, etc. For example, a movable blade may be disposed within the distal end of the hollow elongated member near the opening in the hollow elongated member. When the empyema enters the opening of the hollow elongated member, it is cut by the movable blade (e.g., rotating blade, oscillating blade, etc.) as it is suctioned by the movable blade. The speed and configuration of the blade may vary and may affect the size and consistency of the empyema that has been cut by the blade. The empyema is then suctioned along the inside of the hollow elongated member to the proximal end of the hollow elongated member. The empyema that exits the proximal end of the hollow elongated member is deposited into a depository within the suction source, for example. Embodiments including the separating members discussed above, as well as the movable blade, provide extra assurances that the empyema will be cut sufficiently to minimize any occlusion or clogging of the openings and/or lumens of the elongated members.

In certain embodiments, the methods comprise delivering gas to the pleural cavity via a delivery member. For example, in some instance, a delivery member may be provided adjacent the outer elongated member and may connect to gas source coupled to the proximal end of the device. For example, in some instances, carbon dioxide ($CO_2$) is delivered to the pleural cavity via the delivery member that terminates at the distal end of the outer elongated member. The delivery member may be coupled to the outside of the outer elongated member—e.g., adjacent to the outer elongated member and/or additional elongated member used for lighting and/or visualization. In some embodiments, the delivery member is disposed within the outer elongated member along with the hollow elongated member.

In certain embodiments, methods of removing empyema from a pleural cavity of a human or veterinary patient using an empyema removal device, such as the one described above, comprise providing suction to a hollow elongated member of the above mentioned empyema removal device; receiving empyema within an opening at the distal end of the outer elongated member; receiving empyema within an opening within the hollow elongated member; cutting the empyema with a movable blade; and suctioning the resulting empyema within the hollow elongated member. In certain embodiments, the methods also include penetrating the empyema with separating members as it enters the opening in the distal end of the outer elongated member. In certain embodiments, the methods also include lighting the pleural cavity and providing video or photographic images on a monitor.

Systems

Aspects of the present disclosure include a system for removing empyema from a pleural cavity of a human or veterinary patient. The systems include an empyema removal device, such as described above, and a suction source that operatively couples to the empyema removal device to provide suction to the empyema removal device. As described above, the suction source may couple to the proximal end of the hollow elongated member of the empyema removal device. In certain embodiments, the system may include an actuating source, such as a motor, that operatively couples to the empyema removal device to provide movement to a movable blade on the empyema removal device. In certain embodiments, the system may include a light source that removably couples to the empyema removal device to provide light at the distal end of the empyema removal device. The light source may include an LED or other light emitting device that provides light that is transmitted to the distal end of the device—e.g., via an optical fiber. Alternatively, the light source may be implemented as a power source that provides electrical power to an LED or other light emitting device disposed at the distal end of the device—e.g., via an electrical conductor, such as a wire, that is extended along or within an elongated member of the device.

In certain embodiments, the system includes a camera device that is coupled to the empyema removal device. The camera source may include a camera or image sensor that receives light from an optical fiber and lens disposed at the distal end of the outer elongated member. The camera source converts the light into images or digital representation of images to be displayed on a monitor or other viewing device. The monitor may also be directly coupled to the empyema removal device (e.g., via a cable) or wirelessly coupled to the camera source, for example.

In certain embodiments, the system includes a gas source that couples to the empyema removal device and provides gas (e.g., carbon dioxide) to be delivered to the pleural cavity. In certain embodiments, the system includes an actuating source, such as a motor, that is coupled to the empyema removal device to provide power and movement to the movable blade at the distal end of the device. It should be appreciated that one or more of the various devices described above that are coupled to the empyema removal device may be combined within a single device.

Figure 13:
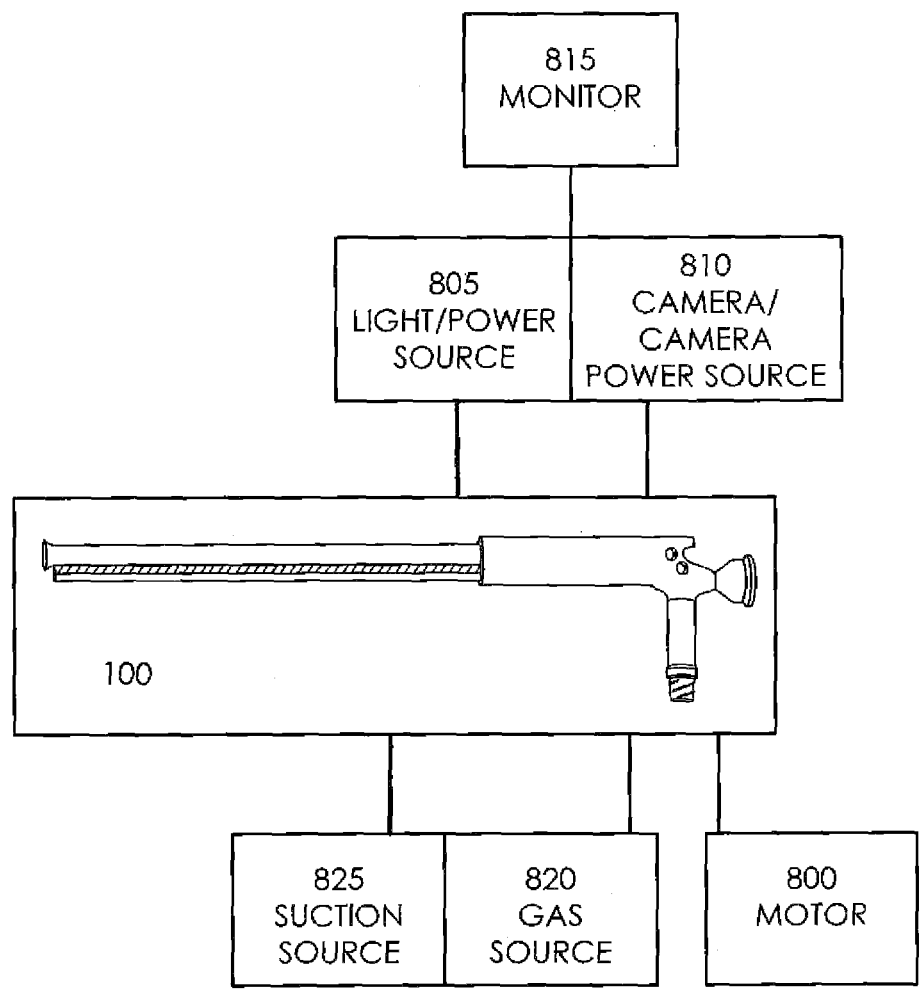
FIG. 13 illustrates a block diagram of a system for removing empyema from a pleural cavity of a human or veterinary patient, according to certain embodiments.

FIG. 13 illustrates a block diagram of a system for removing empyema from a pleural cavity of a human or veterinary patient, according to certain embodiments. As shown, empyema removal device 100, such as the ones described above, is coupled to an actuating source 800 (e.g., a motor) and/or suction source 825 via coupling element 155; light source 805 (or light power source) via coupling element 150; camera device 810 (or camera power source) via viewing lens 165; and gas source 820 via coupling element 166. Empyema removal device is also coupled to monitor 815 via camera source 810, which is in communication with monitor 815.

Utility

The subject devices, systems, and methods find use in a variety of different applications where empyema is removed from a pleural cavity of a human or veterinary subject. In certain embodiments, the devices, systems, and methods are directed to removing empyema from a pleural cavity of a patient that has resulted from pneumonia.

Removal of empyema from the pleural cavity of a subject patient enables the lung of a patient to properly expand without obstruction or interference from the empyema, and thus alleviating associated symptoms such as difficulty breathing and hardening of the lungs.

The subject devices, systems, and methods enable a minimal incision to be made to reduce pain and recovery time endured by patients. Further, they enable an operator of the device to view the pleural cavity while maneuvering the device within the pleural cavity. They also allow fewer ports to be used since components are provided on the device—e.g., lighting, visualization, suction, gas delivery. Still further, they reduce the likelihood of empyema occluding the device. For example, a movable blade and separating members may be implemented to reduce the likelihood of occlusion. Still further, potential damage to untargeted tissues is reduced. The various shapes and configurations of the distal end of the device described above provide additional protection from untargeted tissue being damaged accidently. The Kits Also provided are kits for use in practicing the subject methods, where the kits may include one or more of the above empyema removal devices described above. The kit may also include one or more additional devices, such as the ones described above, that couple to the empyema removal device to provide additional functionality. As such, a kit may include one or more of the following devices: a light source (or power source for a light), a camera device (or power source for a camera), a gas source, a monitor, suction source, and actuating source. In some instances, the kit may include connecting elements that couple the empyema removal device and the additional devices—e.g., hoses, cables, etc. Furthermore, the kits may include, in some instances, products used to sterilize or otherwise clean the device and/or body of the patient. Various components may be packaged as desired, e.g., together or separately.

In addition to above mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Although the foregoing embodiments have been described in some detail by way of illustration and example for purposes of clarity of understanding, it is readily apparent to those of ordinary skill in the art in light of the teachings of the present disclosure that certain changes and modifications may be made thereto without departing from the spirit or scope of the appended claims. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

The invention claimed is:

1. A device for removing empyema from a pleural cavity of a human or veterinary patient, comprising:
    a hollow elongated member having a proximal end and a distal end, the hollow elongated member adapted to couple to a suction source at the proximal end and to enable suction at the distal end of the hollow elongated member, the hollow elongated member having a first opening at the distal end;
    a movable blade disposed within the hollow elongated member, the movable blade configured to move such that empyema suctioned through the first opening is cut by the blade; and
    an outer elongated member disposed around the hollow elongated member, the outer elongated member having a distal end extending past the distal end of the hollow elongated member such that the distal end of the hollow elongated member is within the outer elongated member and is adapted such that, in use, the outer elongated member contacts target empyema before the hollow elongated member and shields or prevents untargeted tissues from entering the opening of the hollow elongated member and contacting the movable blade;
    a second opening at the tip of the distal end of the outer elongated member, wherein the distal end of the outer elongated member is configured such that suction from the hollow elongated member is provided at the second opening; and
    at least one separating member extending across the second opening and attached to the perimeter of the second opening, and/or a pressure relief element comprising a notch or a protrusion on the perimeter of the second opening.

2. The device of claim 1, wherein the outer elongated member and the hollow elongated member are tubular, and wherein a longitudinal axis of the outer elongated member is coaxial with a longitudinal axis of the hollow elongated member.

3. The device of claim 1, comprising a lighting element disposed at a distal end of the device.

4. The device of claim 3, wherein the lighting element is an LED or optical fiber.

5. The device of claim 1, comprising a visualization element disposed at a distal end of the device.

6. The device of claim 5, wherein the visualization element is a camera or lens.

7. The device of claim 1, comprising a delivery member for delivering gas to a distal end of the device.

8. The device of claim 7, wherein the delivery member is formed adjacent to the outer elongated member.

9. The device of claim 1, wherein the distal end of the outer elongated member is flared.

10. The device of claim 1, comprising:
    at least one separating member extending across the second opening and attached to the perimeter of the second opening of the outer elongated member;
    a lighting element disposed at a distal end of the device; and
    a visualization element disposed at the distal end of the device.

11. The device of claim 10, wherein the lighting element is an LED or optical fiber.

12. The device of claim 11, wherein the visualization element is a camera or lens.

13. The device of claim 10, comprising a delivery member for delivering gas to the distal end of the device.

14. The device of claim 10, wherein the distal end of the outer elongated member is flared.

15. The device of claim 10, wherein the outer elongated member includes a pressure relief element comprising a notch or a protrusion on the perimeter of the second opening.

16. The device of claim 10, wherein the distal end of the outer elongated member is angled.

17. The device of claim 10, wherein the distal end of the outer elongated member is removably coupled to a remainder of the outer elongated member.

18. The device of claim 1, wherein the distal end of the outer elongated member is angled.

19. The device of claim 1, wherein the distal end of the outer elongated member is removably coupled to a remainder of the outer elongated member.

20. A system for removing empyema from a pleural cavity of a human or veterinary patient, comprising:
    a device according to claim 1;
    an actuating source coupled to the device to activate movement of the movable blade; and
    a suction source coupled to the device to provide suction to the hollow elongated member of the device.

21. The system of claim 20, comprising:
    a gas source coupled to the device, wherein the device comprises a delivery member for delivering gas to a distal end of the device, and wherein the gas source is coupled to the gas delivering lumen.

22. The system of claim 21, wherein the delivery member is adjacent to the outer elongated member.

23. The system of claim 20, comprising a monitor communicatively coupled to the device to display images of the pleural cavity.

24. The system of claim 20, comprising a camera source coupled to the device, the camera source receiving light via an optical fiber and lens disposed at a distal end of the device, the camera source converting the light into images or digital representations of images.

25. A kit comprising;
    a device according to claim 1, wherein the distal end of the outer elongated member is removably coupled to a remainder of the outer elongated member; and
    one or more additional distal ends that removably couple to the remainder of the outer elongated member.

26. The kit of claim 25, comprising:
    an actuating source removably couplable to the device, the actuating source to activate movement of the movable blade when coupled; and
    a suction source removably couplable to the hollow elongated member, the suction source to provide suction within the hollow elongated member when coupled.

27. The kit of claim 26, comprising:
    a gas source removably couplable to the device, wherein the device comprises a delivery member for delivering gas to a distal end of the device, and wherein the gas source is removably couplable to the delivery member.

28. The kit of claim 27, wherein the delivery member is adjacent to the outer elongated member.

29. The kit of claim 25, comprising a monitor to display images of the pleural cavity when communicatively coupled.

30. A method for removing empyema in a pleural cavity of a human or veterinary patient, the method comprising:
    inserting a distal end of an empyema removal device according to claim 1 into a pleural cavity of a human or veterinary patient;
    advancing the distal end of the device towards empyema;
    suctioning the empyema into the second opening of the outer elongated member and into the first opening of the hollow elongated member;
    cutting the empyema with a movable blade as the empyema is suctioned past the movable blade, the movable blade disposed within the distal end of the hollow elongated member.

31. The method of claim 30, comprising:
    emitting light into the pleural cavity from a lighting element disposed at the distal end of the device; and
    displaying photographic or video images of the pleural cavity on a monitor or viewing device.

32. The method of claim 31, wherein the outer elongated member includes at least one separating member extending across and attached to the perimeter of the second opening of the outer elongated member such that empyema suctioned within the second opening is penetrated by the at least one separating member.

33. The method of claim 32, wherein the distal end of the outer elongated member is flared.

34. The method of claim 31, comprising delivering gas to a distal end of the device via a delivery member.

35. The method of claim 34, wherein carbon dioxide is delivered to the distal end of the device to inflate the pleural cavity of the patient.

36. The method of claim 31, wherein the suctioning is activated and deactivated by a trigger element on the device.

37. The method of claim 31, comprising suctioning the empyema into a depository coupled to a proximal end of the device.

38. The method of claim 30, wherein the distal end of the outer elongated member is removably coupled to a remainder of the outer elongated member, and wherein the method comprises:
    removing the distal end of the outer elongated member from the remainder of the outer elongated member; and coupling a new distal end to the remainder of the outer elongated member.

39. A device for removing empyema from a pleural cavity of a human or veterinary patient, comprising:
- a hollow elongated member having a proximal end and a distal end, the hollow elongated member adapted to couple to a suction source at the proximal end and to enable suction at the distal end of the hollow elongated member, the hollow elongated member having a first opening at the distal end;
- a movable blade disposed within the hollow elongated member, the movable blade configured to move such that empyema suctioned through the first opening is cut by the blade; and
- an outer elongated member disposed around the hollow elongated member, the outer elongated member having a distal end extending past the distal end of the hollow elongated member such that the distal end of the hollow elongated member is within the outer elongated member;
- a second opening at the tip of the distal end of the outer elongated member, wherein the distal end of the outer elongated member is configured such that suction from the hollow elongated member is provided at the second opening; and
- at least one separating member extending across the second opening and attached to the perimeter of the second opening.

40. The device according to claim 39, wherein the outer elongated member comprises a pressure relief element comprising a notch or a protrusion on the perimeter of the second opening.

41. The device according to claim 39, wherein the outer elongated member and the hollow elongated member are tubular, and wherein a longitudinal axis of the outer elongated member is coaxial with a longitudinal axis of the hollow elongated member.

42. The device according to claim 39, comprising a lighting element disposed at a distal end of the device.

43. The device according to claim 42, wherein the lighting element is an LED or optical fiber.

44. The device according to claim 39, comprising a visualization element disposed at a distal end of the device.

45. The device according to claim 44, wherein the visualization element is a camera or lens.

46. The device according to claim 39, comprising a delivery member for delivering gas to a distal end of the device.

47. The device according to claim 46, wherein the delivery member is formed adjacent to the outer elongated member.

48. The device according to claim 39, wherein the distal end of the outer elongated member is flared.

* * * * *